(12) United States Patent
Braess

(10) Patent No.: US 7,807,987 B2
(45) Date of Patent: Oct. 5, 2010

(54) DEVICE AND METHOD FOR LOCALLY RESOLVED CONTROL OF A RADIATION DOSE

(75) Inventor: Henning Braess, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 662 days.

(21) Appl. No.: 11/805,045

(22) Filed: May 22, 2007

(65) Prior Publication Data

US 2008/0135764 A1 Jun. 12, 2008

Related U.S. Application Data

(60) Provisional application No. 60/802,870, filed on May 23, 2006.

(30) Foreign Application Priority Data

May 23, 2006 (DE) ........................ 10 2006 024 243

(51) Int. Cl.
*A61N 5/00* (2006.01)
(52) U.S. Cl. ................................. 250/492.3; 250/491.1
(58) Field of Classification Search ... 250/492.1–492.3, 250/493.1–504 H, 396 R–396 ML
See application file for complete search history.

(56) References Cited

U.S. PATENT DOCUMENTS

| 5,272,343 | A | | 12/1993 | Stearns |
| 5,864,146 | A | * | 1/1999 | Karellas ..................... 250/581 |
| 5,939,724 | A | * | 8/1999 | Eisen et al. ............. 250/370.09 |
| 5,998,793 | A | | 12/1999 | Shao et al. |
| 6,294,788 | B1 | | 9/2001 | Cooke et al. |
| 2001/0051766 | A1 | * | 12/2001 | Gazdzinski ................. 600/309 |
| 2002/0070365 | A1 | * | 6/2002 | Karellas ..................... 250/581 |
| 2002/0196899 | A1 | * | 12/2002 | Karellas ..................... 378/98.8 |
| 2003/0179853 | A1 | * | 9/2003 | Amemiya et al. ............. 378/63 |
| 2004/0081277 | A1 | * | 4/2004 | Amemiya et al. ............. 378/63 |
| 2004/0081278 | A1 | * | 4/2004 | Amemiya et al. ............. 378/63 |
| 2005/0082469 | A1 | * | 4/2005 | Carlo ......................... 250/262 |
| 2005/0205791 | A1 | | 9/2005 | Bryman |
| 2006/0113479 | A1 | | 6/2006 | Zavarzin |

(Continued)

FOREIGN PATENT DOCUMENTS

DE 10 2004 009 784 A1 9/2005

(Continued)

OTHER PUBLICATIONS

K.Parodi: "On the feasibility of dose quantification with in-beam PET data in radiotherapy with 12C and proton beams", Dissertation, Dresden, 2004, pp. 35-99, Chapter: 4-5.

(Continued)

*Primary Examiner*—Jack I Berman
*Assistant Examiner*—Andrew Smyth

(57) ABSTRACT

A device for locally resolved control of a radiation dose applied with a pulsed particle beam in particle beam therapy, with a processing unit, which is set up to detect continuously a count rate of x-ray quanta measured with a positron emission tomograph and to determine the applied radiation dose from the pattern of the measured count rate, by determining by computation from the measured pattern of the count rate the time intervals, in which an interaction of the particle beam takes place at the application site and by rejecting these time intervals for the determination of the applied radiation dose.

13 Claims, 4 Drawing Sheets

U.S. PATENT DOCUMENTS

2006/0188059 A1* 8/2006 Amemiya et al. ............. 378/19
2010/0016715 A1* 1/2010 Gagnon et al. ............. 600/436

FOREIGN PATENT DOCUMENTS

EP          1 077 383 A2    2/2001

OTHER PUBLICATIONS

D. Brasse et al.: "Correction methods for random coincidences in fully 3D whole-body PET: Impact on data and image quality", Journal of Nuclear Medicine, May 2005, pp. 859-867, vol. 46, No. 5.

* cited by examiner

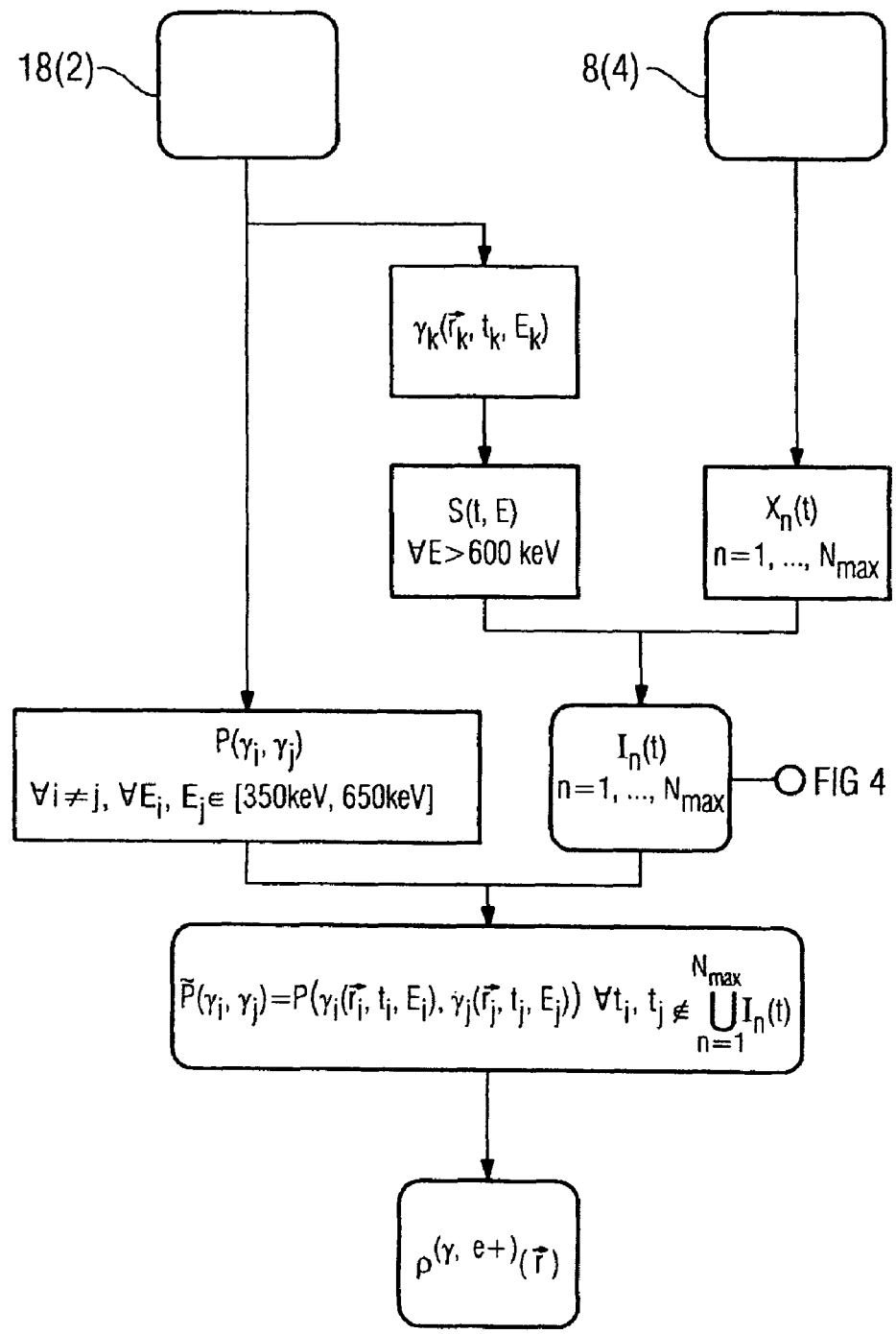

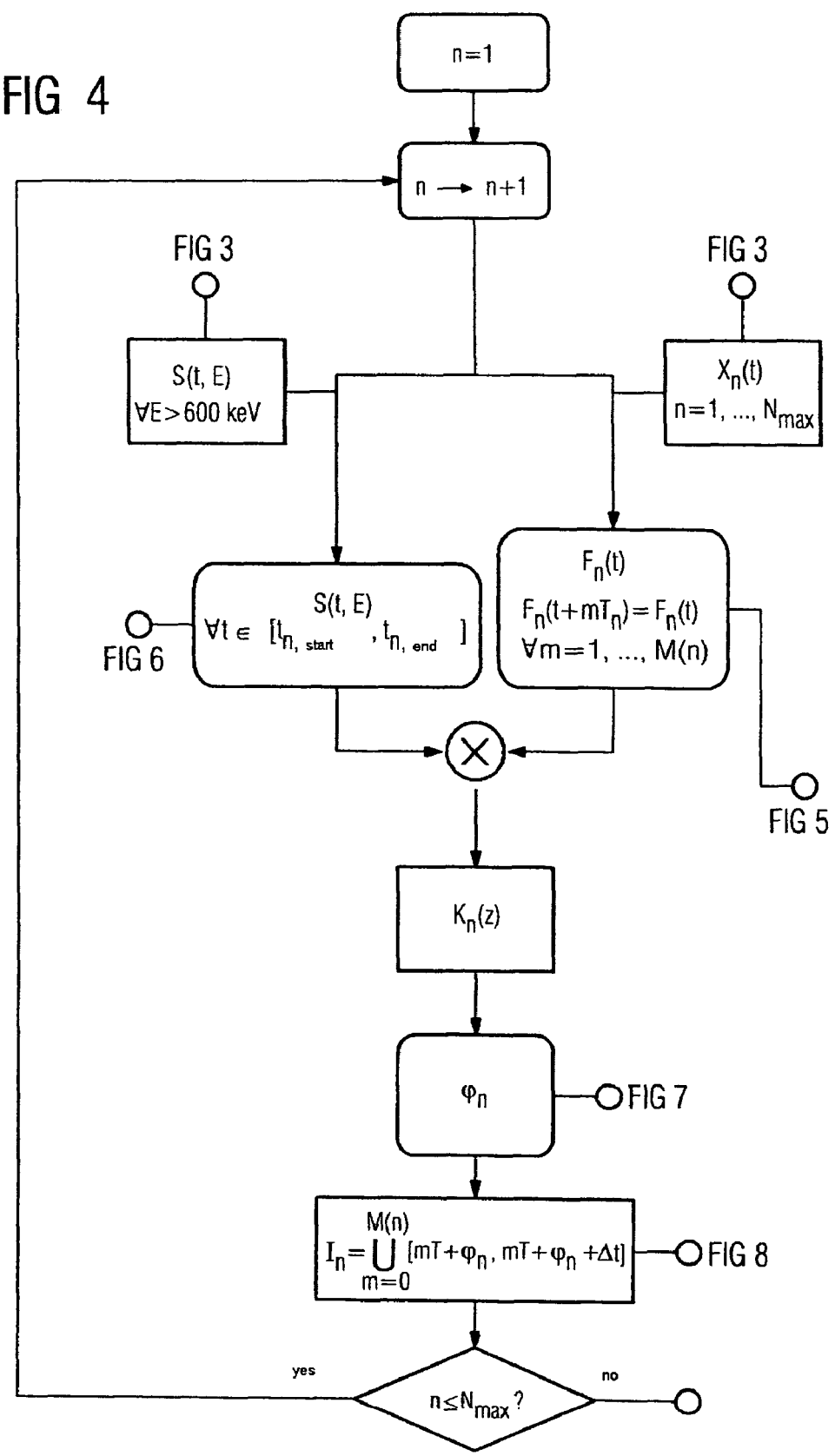

FIG 5
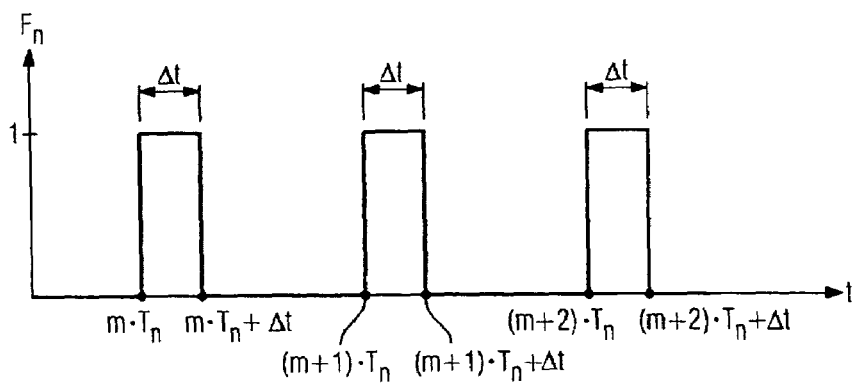

FIG 6
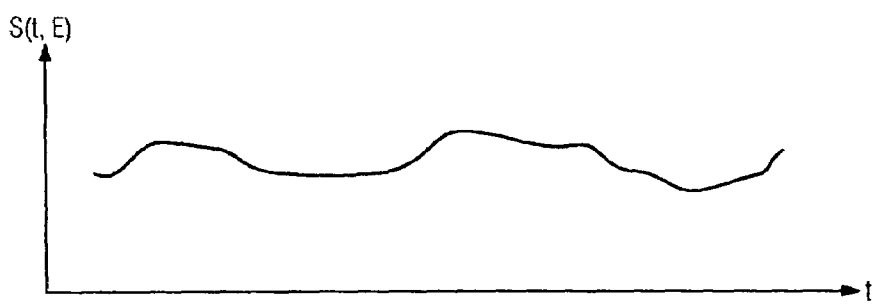

FIG 7
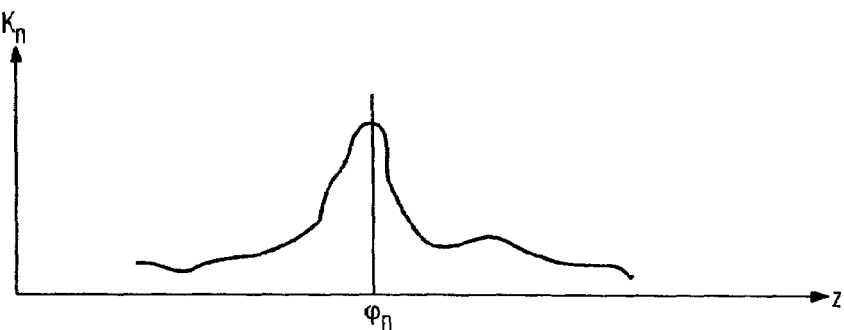

FIG 8

$$I_n^{(m)} = [\varphi_n, \varphi_n + \Delta t]$$
$$\vdots$$
$$I_n^{(m)} = [m \cdot T_n + \varphi_n, m \cdot T_n + \varphi_n + \Delta t]$$
$$I_n^{(m+1)} = [(m+1) \cdot T_n + \varphi_n, (m+1) \cdot T_n + \varphi_n + \Delta t]$$
$$I_n^{(m+2)} = [(m+2) \cdot T_n + \varphi_n, (m+2) \cdot T_n + \varphi_n + \Delta t]$$
$$\vdots$$
$$I_n^{M(n)} = [M(n) \cdot T_n + \varphi_n, M(n) \cdot T_n + \varphi_n + \Delta t]$$

$$I_n = \bigcup_{m=0}^{M(n)-1} I_n^{(m)}$$
$$= \bigcup_{m=0}^{M(n)-1} [mT + \varphi_n, mT + \varphi_n + \Delta t]$$

DEVICE AND METHOD FOR LOCALLY RESOLVED CONTROL OF A RADIATION DOSE

CROSS REFERENCE TO RELATED APPLICATIONS

The present application claims the benefit of the provisional patent application filed on May 23, 2006, and assigned application No. 60/802,870. The present application also claims priority of German application No. 10 2006 024 243.2 filed on May 23, 2006. Both of the applications are incorporated by reference herein in their entirety.

FIELD OF THE INVENTION

The invention relates to a device and method for locally resolved control of a radiation dose applied with a pulsed particle beam in particle beam therapy.

BACKGROUND OF THE INVENTION

In particle beam therapy a tumor in a patient is irradiated with protons or ions in a pulsed manner. This pulsed proton or ion radiation is supplied in this context by a particle accelerator, for example a synchrotron. Radiation pulse sequences, having an infinite number of radiation pulses, alternate here with beam delays. The radiation parameters here are set in such a manner that the greatest degree of destruction possible of the tumor tissue is achieved with the smallest possible degree of damage to the surrounding healthy body tissue. They are determined before the radiation therapy takes place. In order to be able to control the radiation dose applied at the application site or, respectively, at the site of the tumor, the applied radiation dose is determined in a locally resolved manner using a positron emission tomograph. This makes use of the fact that positron emitters are formed at the application site by nuclear conversions during the radiation process. Every positron emitter releases a positron as it decays, said positron together with an electron annihilating with an energy of 511 keV respectively in two x-ray quanta. These x-ray quanta are measured by the positron emission tomograph. An evaluation algorithm is used to determine the respective site of origin of the x-ray quanta from this location information. The radiation dose applied at the application site is calculated in a locally resolved manner by temporally integrating decay events in the radiation period. It is thus possible to verify, in a locally resolved manner, the extent to which the radiation dose actually applied differs from the planned radiation dose. It is thus possible to adapt the radiation parameters for further radiation processes.

The positron emission tomograph has a processing unit, in which two tests are carried out, to establish whether two detected x-ray quanta can be traced back to a positron decay. On the one hand it is verified whether the two x-ray quanta lie in a narrow time window, what is known as a coincidence window, of around 2-10 ns duration. In a second test it is verified whether the x-ray quanta respectively have an energy of 511 keV. Since the accuracy of the energy measurement is limited, x-ray quanta, which originate from am energy window of around 350 keV to 650 keV, are assigned to a positron decay.

A problem arises during the evaluation of the measured x-ray quanta. During the interaction of the particle beam at the application site the energy input due to the protons or ions causes further numerous nuclear reactions to be induced, which similarly result in the emission of x-ray quanta. If two such x-ray quanta lie in a common coincidence window, positron decays are simulated. Therefore the positron emission tomograph is not generally used for measurement purposes during the interaction of the pulsed particle beam with the body tissue. Measuring only takes place in the beam delays between the radiation pulse sequences. Since these beam delays only make up around 30 to 70% of the total beam exposure time, compared with the radiation pulse sequences, also referred to as beam extraction phases, and since positron decays are not taken into account during the beam extraction phases, measuring using positron emission tomographs is subject to relatively major error. This error is perpetuated in the calculation of the radiation dose applied in a site-dependent manner.

Generation of x-ray quanta, which are not attributable to a positron decay, takes place almost exclusively during the interaction of a radiation pulse with the body tissue. The radioactive isotopes occurring in the body tissue in addition to the positron beams are so short-lived that their decay takes place during or immediately after such a radiation pulse. A precise temporal identification of the time intervals, in which the radiation pulses interact with the tumor tissue, would also make it possible to evaluate the coincidence events, which occur in the time intervals between radiation pulses. This would allow a decisive improvement in the evaluation statistics.

The radiation pulse sequence is known, since the particle accelerator receives a corresponding control signal, generated by a control unit, but the protons or ions first cover a free flight distance from the site of origin or reference site in the particle accelerator to the application site, in other words to the tumor to be irradiated, followed by a path inside the body. Since the decay of the radioactive isotopes also takes a specific time, it is not clear from the x-ray quanta measured as a function of time, at which time exactly the interaction of a radiation pulse with the body tissue takes place.

In P. Crespo et. al., "Suppression of Random Coincidences During In-Beam PET Measurements at Ion Beam Radiotherapy Facilities", IEEE Transactions on Nuclear Science, Vol. 52, 2005, page 980 ff two methods are proposed for determining the times of the radiation pulses and therefore the times of the delays between the radiation pulses.

With the first method an additional detector in the beam path is used to measure when a radiation pulse occurs. Since the additional detector is disposed close to the application site, there is only a small time offset between the detector site and the application site. Very precise synchronization is required here between the measurement signals measured by the positron emission tomograph and the measurement signals of the additional detector. This requires a complex electronic unit.

With the second measuring method the control signals, with which the particle accelerator is triggered by way of the control unit, are evaluated. The radiation pulse sequence is therefore known. An electrical component, what is known as a phase trigger, is used to determine the delay between the reference site and the application site. This method also requires very complex and precise synchronization between the control signal of the particle accelerator and the positron emission tomograph.

With both methods described those time intervals are determined, in which an interaction takes place with the particle beam at the application site. Those coincidence events, the recording time of which lies in such an interval, are then rejected, in other words not used for an evaluation. Determination of the time intervals is however very complex in both instances.

SUMMARY OF THE INVENTION

The object of the invention is to allow a locally resolved detection of the applied radiation dose in a simple and economical manner.

According to the invention this object is achieved by the feature combination in the claims.

The inventive device comprises a processing unit, which is used to register x-ray quanta measured using a positron emission tomograph as a function of time, location and energy. The time intervals, during which an interaction of the particle beam takes place at the application site, are first determined from this count rate. A coincidence unit is also used to determine which of the x-ray quanta lie in a narrow time window, what is known as a coincidence window, and represent what are known as coincidence events. In general a beam-induced positron concentration is measured with the aid of the positron emission tomograph.

Those coincidence events, which were measured temporally in one of the determined time intervals, are then rejected for the determination of the applied radiation dose. The applied radiation dose is then calculated from the remaining coincidence events. This is a purely software-based solution, which determines the radiation pulse sequence based on the count rate of x-ray quanta that is measured in any case. Such a solution can be implemented in a simple and economical manner. Complex calibration operations, as required with a hardware-based solution, do not have to be implemented here. Nor is there any need for a complex additional technical measuring arrangement.

The processing unit is preferably set up to evaluate the beam delays between the individual radiation pulse sequences to control the applied radiation dose. Since the time intervals between the individual beam pulses are also evaluated, the evaluation is carried out over almost the entire radiation period. This results in a clear improvement in respect of the count statistics. The measurement error, to which the determination of the locally resolved, applied radiation dose is subject, is significantly reduced compared with the former procedure, in which only the beam delay periods were evaluated.

In one development the processing unit is set up to determine a time offset of the radiation pulse sequence at the application site in relation to the time of its generation. This time is predetermined for example by a control unit, which generates a control signal to generate the radiation pulse sequence. The temporal pattern of the radiation pulse sequence is known. The corresponding information is forwarded from the control unit to the processing unit. The processing unit computes this radiation pulse sequence with the temporal pattern of the count rate of characteristic decay events, which are measured as characteristic detector events. Those decay events, which occur either only or particularly frequently during the interaction of a radiation pulse with the body tissue, are selected here from the sum of all the decay events measured using the detectors of the positron emission tomograph.

The time offset of the radiation pulse sequences at the application site gives the time intervals, at which the individual radiation pulses interact with the tumor tissue and in which many further x-ray quanta are generated in addition to x-ray quanta from positron decay. Coincidence events, which are measured in these time periods, are not used for the evaluation.

The processing unit is preferably set up here to determine the time offset, by simulating the radiation pulse sequence at the time of its generation by means of a periodic function. This function is computed with the temporal pattern of the count rate of the characteristic decay events. This gives the time offset. Simulation of the radiation pulse sequence by a periodic function is very simple to implement. In the simplest instance it is a rectangular function, having a constant value during the period of a radiation pulse and being otherwise zero.

In an expedient variant the processing unit is set up to determine the time offset by forming a mathematical correlation function from the periodic function and the temporal pattern of the count rate of the characteristic decay events, said mathematical correlation function for example having the appearance of a convolution integral. The time offset of the radiation pulse sequence at the application site compared with the time of its generation is then clear from the maximum of the correlation function. The formation of a correlation function is a method known anyway in mathematics, which is easy to convert for programming purposes. It is thus possible to determine the time offset in a particularly simple manner.

Individual decay events are for example suitable for the selection of the characteristic decay events characterizing the interaction of a radiation pulse with the body tissue. In this context the temporal patterns of individual decay events are preferably analyzed, their energy significantly exceeding the energy of an x-ray quantum generated from the decay of a positron. This ensures that x-ray quanta generated during positron decay are not used inadvertently for the evaluation. This would be possible for example, if only one of the two x-ray quanta was detected by a detector, while the second x-ray quantum was absorbed by body tissue.

Suitable characteristic decay events are also decay events comprising two or three x-ray quanta in one coincidence window. In this process both real coincidences during the decay of a positron are detected as well as random coincidences, when for example a single x-ray quantum and an x-ray quantum resulting from a positron decay are detected together in the coincidence window.

All these decay events described have in common the fact that they occur with particular frequency during the interaction of a radiation pulse with the body tissue. By forming a correlation function with the periodic function, it is possible to determine the time offset of the radiation pulse at the application site reliably from the temporal pattern of the count rate of said characteristic decay events, where there is sufficient radiation intensity. The extraction of said characteristic decay events from the totality of all decay events detected by the processing unit is achieved in a simple manner using a sorting algorithm. Information about the temporal pattern of characteristic decay events is thus easy to access. To improve the evaluation it is also possible to consider the count rates of different groups of said characteristic decay events in combination.

In one development the processing unit uses all the characteristic events in a specific energy window to determine the offset time. This energy window can be adjusted by programming in such a manner that the correlation function shows a clear maximum. This allows the offset time to be determined in a reliable manner. The single adjustment of the energy window during a commissioning phase is simple and uncomplicated to implement.

According to the invention the object is also achieved by a method as claimed in the claims. Further advantageous embodiments will emerge from the subclaims dealing with a method. The advantages and preferred embodiments specified in respect of the device should be applied appropriately thereto.

BRIEF DESCRIPTION OF THE DRAWINGS

An exemplary embodiment of the invention is described in more detail below with reference to a drawing, in which:

FIG. 3 shows a schematic diagram of an evaluation system for the locally resolved determination of the applied radiation dose, FIG. 4 shows a schematic diagram of an evaluation algorithm to determine the time intervals, in which radiation pulses occur at the application site, FIG. 5 shows a periodic rectangular function, FIG. 6 shows the temporal pattern of a count rate of characteristic decay events, FIG. 7 shows a correlation function formed from the functions illustrated in FIG. 5 and FIG. 6, and FIG. 8 shows a list of those time intervals of a beam pulse sequence, in which an interaction of the particle beam takes place at the application site.

DETAILED DESCRIPTION OF THE INVENTION

Figure 1:
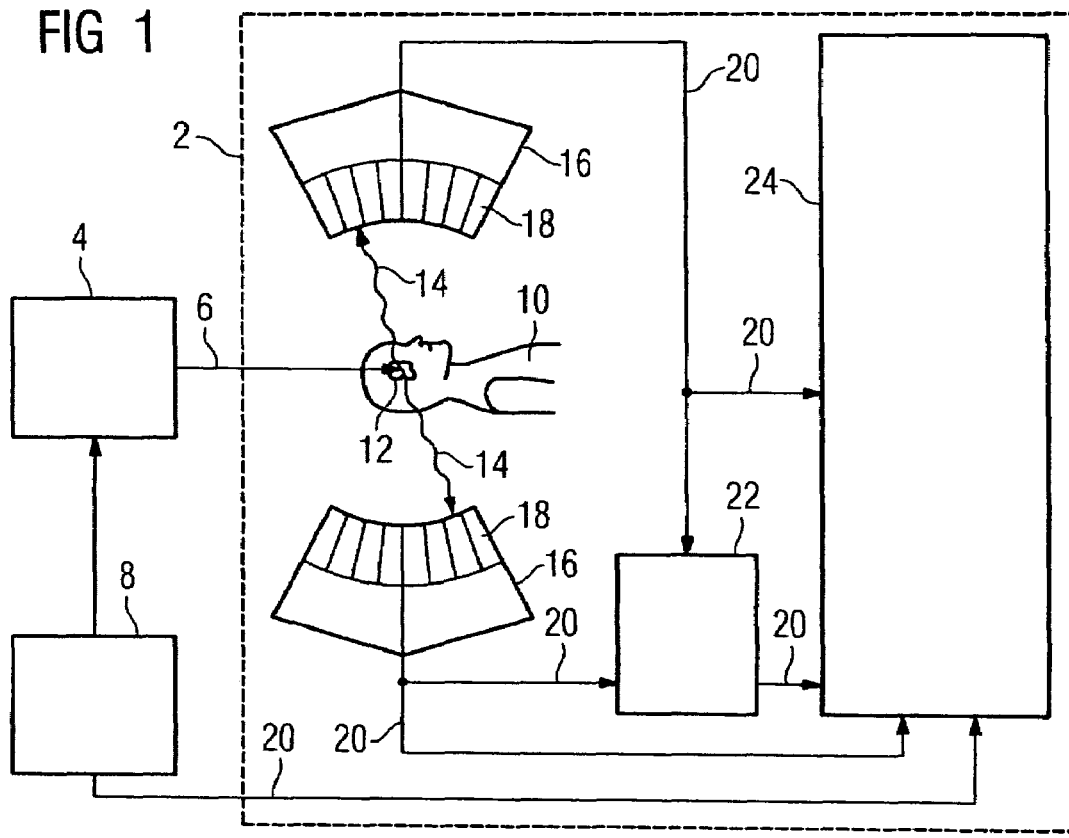
FIG. 1 shows a schematic diagram of a device for particle beam therapy with a positron emission tomograph for locally resolved control of an applied radiation dose.

FIG. 1 shows a schematic diagram of a device for particle beam therapy, having a positron emission tomograph 2 for locally resolved control of an applied radiation dose. For particle beam therapy a particle accelerator 4 generates a pulsed particle beam 6. This pulsed particle beam 6 contains protons or ions. Its pulse sequence is predetermined by a control unit 8. The pulsed particle beam 6 is used to irradiate tumor tissue 12 in a person 10 in a specific manner. Radiation causes positron emitters to form at the application site, in other words within the tumor tissue 12 and these decay very quickly, emitting a positron in each instance. Each of these positrons annihilates with an electron of an adjacent atom, in that two x-ray quanta 14 fly out from the annihilation site in opposing directions, in other words at a 180° angle. The two x-ray quanta 14 are registered respectively by one of the detectors 18 disposed in a circle round the application site and held by a holding device 16. Two measurement signals are generated in this process, which are verified by means of two measuring lines 20 first for their coincidence, in other words their quasi-simultaneity, in a coincidence unit 22. All decay events are also registered in a processing unit 24 by ways of the measuring lines 20. The data is stored in a data storage unit there, with the energy of each x-ray quantum 14, its time of registration and the registering detector 18 being detected. The registering detector 18 holds the location information of the x-ray quantum 14.

In the processing unit 24 position decay events are assigned to the x-ray quanta 14 measured in coincidence. The location information of the detectors 18 thus allows conclusions to be drawn about the decay site in the tumor tissue 12. The applied radiation dose is calculated in a locally resolved manner by means of integration over the radiation period. The calculated radiation dose is compared with the radiation dose predetermined by the control unit 8 in the context of the radiation therapy schedule. This comparison serves to control the particle beam therapy and allows adjustment of future radiation sessions.

Figure 2:
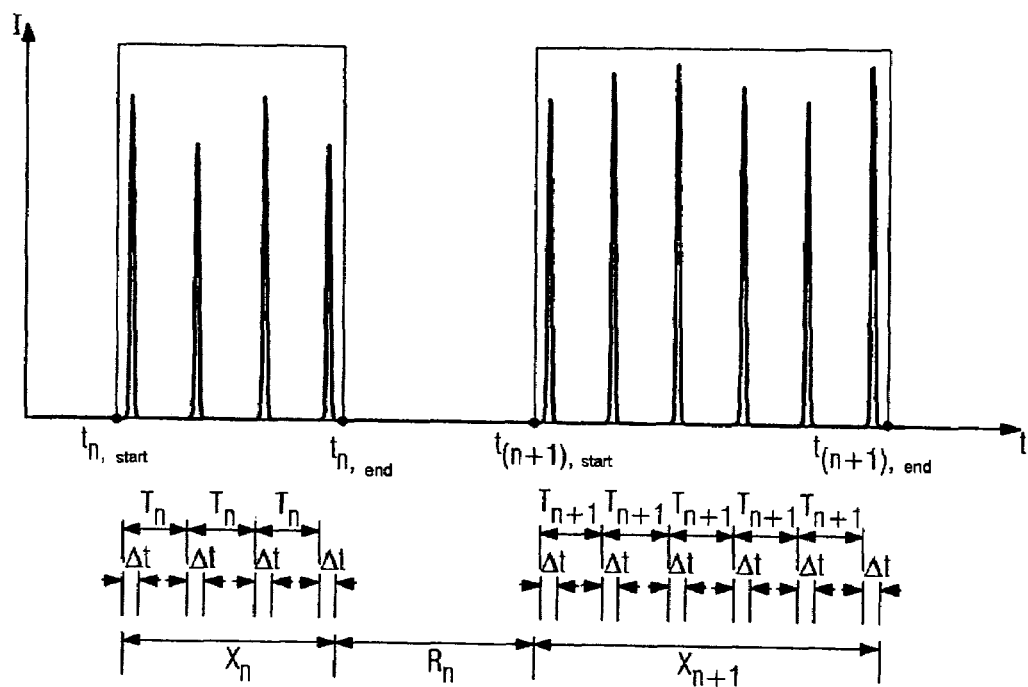
FIG. 2 shows a time-intensity diagram of a particle beam with two radiation pulse sequences and a beam delay therebetween.

FIG. 2 shows the intensity pattern of the pulses particle beam 6 as a function of time. It shows two pulse sequences $X_n$ and $X_{n+1}$, between which there is a beam delay R. The continuous index n here runs from 1 to a maximum value $N_{max}$. Thus a total of $N_{max}$ radiation pulse sequences are considered. Both radiation pulse sequences have a start point $t_{n,start}$ and/or $t_{n+1,start}$ and an end point $t_{n,end}$ and/or $t_{n+1,end}$. The radiation pulse sequence $X_n$ comprises a total of four radiation pulses with a pulse length of $\Delta t$ and a period of $T_n$. The radiation pulse sequence $X_{n+1}$ comprises six radiation pulses with a pulse length of $\Delta t$ and a period of $T_{n+1}$. In practice radiation pulse sequences and beam delays alternate over the entire period of irradiation of the tumor tissue 12. Radiation pulse sequences typically have a duration of around 1 to 10 seconds and beam delays a duration of 1 to 3 seconds. The individual radiation pulses typically have from 1 to 1,000 particles and a length of around 10 to 100 ns. The period length $T_n$ and thus the time difference between two adjacent radiation pulses is several 100 ns. In practice a radiation pulse sequence comprises significantly more than four or six radiation pulses. FIG. 2 is simply an idealized illustration.

FIG. 3 shows how the locally resolved determination of the applied radiation dose takes place. The detectors 18 of the positron emission tomograph 2 detect decay occurring in a narrowly dimensioned time window of several ns, known as coincidence events, by means of the coincidence unit 22. The formula $$P(\gamma_i,\gamma_j)=P(\gamma_i(\vec{r}_i,t_i,E_i),\gamma_j(\vec{r}_j,t_j,E_j)), \ i \neq j$$

shows that these coincidence events contain location, time and energy information for two different ($i \neq j$) x-ray quanta $\gamma_i$, $\gamma_j$.

The detectors 18 also detect all the x-ray quanta $\gamma_k(\vec{r}_k,t_k,E_k)$ with their location, time and energy information. Characteristic decay events $S(t,E)$ are selected from among these x-ray quanta $\gamma_k$. These are x-ray quanta 14 with an energy significantly exceeding the energy for a positron decay of 511 keV. The count rate of these characteristic decay events $S(t,E)$ is considered in respect of its time-dependent pattern.

Characteristic decay events, which comprise two or three x-ray quanta in one coincidence window, can however also be evaluated by way of example. Groups of characteristic decay events $S(t,E)$ can also be considered in a common manner.

The control unit 8 of the particle accelerator 4 transmits information by way of a measuring line 20 to the processing unit 24 regarding the period $T_n$ and pulse duration $\Delta t$ used to generate control signals for a radiation pulse sequence $X_n$.

The characteristic decay events $S(t,E)$ and radiation pulse sequences $X_n$ are used to determine, by way of a method still to be described, those time intervals $I_n$, at which an interaction of the corresponding radiation pulses takes place at the application site, in the tumor tissue 12.

The only coincidence events $P(\gamma_i,\gamma_j)$ considered further are those whose two x-ray quanta have an energy between 350 keV and 650 keV:

$$P(\gamma_i,\gamma_j)=P(\gamma_i(\vec{r}_i,t_i,E_i),\gamma_j(\vec{r}_j,t_j,E_j)) \ \forall E_i,E_j \in [350 \text{ keV}, 650 \text{ keV}].$$

Since the x-ray quanta lose energy in the body tissue, at the time of registration their energy is less than the energy value of 511 keV characteristic of a positron decay at the site of origin of the two x-ray quanta.

These coincidence events are sought out from the totality of all coincidence events in the processing unit 24 by means of a sorting algorithm.

Of the coincidence events $P(\gamma_i,\gamma_j)$ those, for which at least one of the two registered times $t_i$ and $t_j$ lies in one of the intervals $I_n$, are rejected. This leaves the events $$\tilde{P}(\gamma_1, \gamma_j) = P(\gamma_i(\vec{r}, t_i, E_i), \gamma_j(\vec{r}_j, t_j, E_j)) \ \forall \ t_i, t_j \notin \bigcup_{n=1}^{N_{\max}} I_n(t).$$

From the remaining coincidences $\tilde{P}(\gamma_i,\gamma_j)$ the radiation dose $\rho^{(\gamma,e+)}(\vec{r})$ applied over the radiation period is determined in a locally resolved manner by integration over the entire radiation time:

$$\rho^{(\gamma,e+)}(\vec{r}) = K(e+) \cdot \int_{t_{start}}^{t_{end}} \Sigma(\tilde{P}(\gamma_1, \gamma_2))\bigg|_{\vec{r}} \cdot dt$$

Here $\Sigma(\tilde{P}(\gamma_1,\gamma_2))|_{\vec{r}}$ designates the totality of all registered positron decays at the site $\vec{r}$, $K(e+)$ a factor specifying the radiation dose resulting from a single positron decay $\tilde{P}(\gamma_i,\gamma_j)$, $t_{start}$ the start and $t_{end}$ the end of the radiation process.

The indexing $(\gamma,e+)$ shows that the x-ray quanta are from a positron decay.

Since the radiation pulses only make up a very short time period in relation to the radiation time, the coincidence events $\tilde{P}(\gamma_i,\gamma_j)$ constitute almost [lacuna] occurring coincidence events. This results in very precise measurement of the radiation dose $\rho^{(\gamma,e+)}(\vec{r})$ applied in a locally resolved manner.

FIG. 4 shows the algorithm for determining those intervals, in which the radiation pulses interact with the tumor tissue 12. The continuous index n again identifies the individual radiation pulse sequences. These radiation pulse sequences are considered in order from the first (n=1) to the last (n=$N_{max}$). The information relating to the respective period $T_n$ of the M(n) radiation pulses within the radiation pulse sequence $X_n$ and the radiation pulse duration $\Delta t$ is simulated with the aid of a periodic function $F_n(t)$. Here $$F_n(t) = F_n(t + mT_n) \ \forall m = 1, \ldots, M(n),$$

in other words the periodic function $F_n(t)$ has the period $T_n$. This gives a series of a total of M(n) identical segments of the function $F_n(t)$ on the time axis.

Such a periodic function $F_n(t)$ is shown in FIG. 5. This is a step function, which assumes the value 1 for the time, during which a radiation pulse is emitted, and is otherwise zero, as set out in the formal equation $$F_n(t) = \begin{cases} 1 & \text{if } t \in [mT_n, mT_n + \Delta t], m = 0, \ldots, M(n) \\ 0 & \text{otherwise} \end{cases}.$$

Generally the periodic function $F_n(t)$ is computed with the time-dependent count rate of characteristic events $S(t,E)$ by way of a convolution. The resulting convolution $K_n(z)$ is determined over the period from the start $t_{n,start}$ to the end $t_{n,end}$ of the radiation pulse sequence:

$$K_n(z) = \int_{t_{n,start}}^{t_{n,end}} S(t) \cdot F_n(t-z) dt$$

The convolution $K_n(z)$ then accurately provides a clear maximum $\phi_n$, when the count rate of the characteristic decay events $S(t,E)$ correlates with the periodic function $F_n(t)$.

This situation is shown by way of example in FIG. 7. An evaluation of the maximum in the convolution space provides the time offset $\phi_n$.

The temporal displacement of the radiation pulses at the application site compared with the reference site results from this time offset $\phi_n$.

FIG. 8 shows the actual time intervals $I_n$ determined from a complete radiation pulse sequence $X_n$ for the interaction of the radiation pulses with the tumor tissue 12. For each individual radiation pulse of the total M(n) of radiation pulses an interval of pulse length $\Delta t$ results with $$I_n^{(m)} = [m \cdot T_n + \phi_n, m \cdot T_n + \phi_n + \Delta t] \ \forall m = 0, \ldots, M(n)-1.$$

The interval $I_n$ is obtained by combining all M(n) intervals $I_n^{(m)}$ to give $$I_n = \bigcup_{m=0}^{M(n)-1} [m \cdot T_n + \varphi_n, m \cdot T_n + \varphi_n + \Delta t]$$

This sequence of time intervals $I_n$ is determined for every radiation pulse sequence $X_n$.

The mathematical combination $$\bigcup_{n=1}^{N_{\max}} I_n(t)$$

of all $N_{max}$ time intervals designates all the time segments, which are not to be used for the evaluation. Coincidence events $\tilde{P}(\gamma_i,\gamma_j)$, which lie in one of these intervals $I_n$, are not used to determine the radiation dose $\rho^{(\gamma,e+)}(\vec{r})$ applied in a locally resolved manner over the treatment period.

The invention claimed is:

1. A device for locally resolved controlling a radiation dose applied by a pulsed particle beam comprising a plurality of radiation pulse sequences at an application site of a patient in a particle beam therapy, comprising:
   a processing unit that:
   continuously measures a count rate of an x-ray quanta by a positron emission tomography,
   calculates a time interval from a pattern of the measured count rate during which the pulsed particle beam interacts at the application site for applying the radiation dose at the application site,
   determines the applied radiation dose at the application site from the pattern of the measured count rate excluding the time interval during which the pulsed particle beam interacts at the application site, wherein the applied radiation dose is site dependent, and
   controls the applied radiation dose based on the determination in the particle beam therapy.

2. A method for locally resolved controlling a radiation dose applied by a pulsed particle beam comprising a plurality of radiation pulse sequences at an application site in a particle beam therapy, comprising:
   continuously measuring a count rate of an x-ray quanta by a positron emission tomography;
   computing a time interval from a pattern of the measured count rate during which the pulsed particle beam interacts at the application site for applying the radiation dose at the application site;
   determining the applied radiation dose at the application site from the pattern of the measured count rate by excluding the time interval during which the pulsed particle beam interacts at the application site, wherein the applied radiation dose is site dependent; and controlling the applied radiation dose based on the determination in the particle beam therapy.

3. The method as claimed in claim 2, wherein beam delays between the radiation pulse sequences are evaluated to control the applied radiation dose.

4. A method for locally resolved controlling a radiation dose applied by a pulsed particle beam comprising a plurality of radiation pulse sequences at an application site in a particle beam therapy, comprising:

continuously detecting a count rate of an x-ray quanta by a positron emission tomography;

computing a time interval during which the pulsed particle beam interacts at the application site;

determining the applied radiation dose from a pattern of the count rate by excluding the time interval for the determination; and controlling the applied radiation dose based on the determination in the particle beam therapy, wherein the time interval is computed based on a time offset of each radiation pulse sequence at the application site in relation to an original site of the each radiation pulse sequence.

5. The method as claimed in claim 4, wherein the time offset is determined by simulating the each radiation pulse sequence at the original site mathematically with a periodic function and computing the function with a temporal pattern of characteristic decay events.

6. The method as claimed in claim 5, wherein a mathematical correlation function from the periodic function and the characteristic decay events is generated and the time offset is a maximum of the correlation function.

7. The method as claimed in claim 5, wherein the periodic function is a rectangular function.

8. The method as claimed in claim 5, wherein the characteristic decay events are selected from individual decay events.

9. The method as claimed in claim 5, wherein the characteristic decay events have an energy that significantly exceeds an energy of an x-ray quantum generated by a decay of a positron.

10. The method as claimed in claim 5, wherein the characteristic decay events comprise two or three x-ray quanta that lie in a predetermined time window.

11. The method as claimed in claim 5, wherein a predetermined energy window is adjusted for determining the time offset.

12. The method as claimed in claim 4, wherein beam delays between the radiation pulse sequences are evaluated to control the applied radiation dose.

13. The method as claimed in claim 2, wherein the time interval is computed based on a time offset of each radiation pulse sequence at the application site in relation to an original site of the each radiation pulse sequence.

* * * * *